United States Patent
Katcha et al.

(10) Patent No.: US 9,119,592 B2
(45) Date of Patent: Sep. 1, 2015

(54) INTERLEAVED RESONANT CONVERTER

(71) Applicant: General Electric Company, Schenectady, NY (US)

(72) Inventors: Jason Stuart Katcha, Waukesha, WI (US); Ezana T. Mekonnen, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 231 days.

(21) Appl. No.: 14/016,417

(22) Filed: Sep. 3, 2013

(65) Prior Publication Data

US 2015/0063525 A1 Mar. 5, 2015

(51) Int. Cl.

| | |
|---|---|
| *H05G 1/10* | (2006.01) |
| *A61B 6/00* | (2006.01) |
| *A61B 6/03* | (2006.01) |
| *H05G 1/58* | (2006.01) |
| H05G 1/20 | (2006.01) |
| H02M 3/335 | (2006.01) |
| H02M 7/493 | (2007.01) |

(52) U.S. Cl.
CPC ... *A61B 6/56* (2013.01); *A61B 6/03* (2013.01); *H05G 1/10* (2013.01); *H05G 1/58* (2013.01); *H02M 3/3353* (2013.01); *H02M 7/493* (2013.01); *H05G 1/20* (2013.01)

(58) Field of Classification Search
CPC ............ A61B 6/032; A61B 6/56; H05G 1/10; H02M 7/5387; H02M 3/3353
USPC ................................................ 378/4–20, 101
See application file for complete search history.

(56) References Cited

U.S. PATENT DOCUMENTS

| | | |
|---|---|---|
| 5,546,294 A | 8/1996 | Schutten et al. |
| 5,808,376 A | 9/1998 | Gordon et al. |
| 6,072,856 A | 6/2000 | Van Der Broeck et al. |
| 7,110,488 B2 | 9/2006 | Katcha et al. |
| 2011/0002446 A1 | 1/2011 | Beland |
| 2012/0027161 A1 | 2/2012 | Abenaim et al. |

FOREIGN PATENT DOCUMENTS

| | | |
|---|---|---|
| WO | 0227908 A1 | 4/2002 |
| WO | 2009109902 A2 | 11/2009 |

OTHER PUBLICATIONS

Search Report and Written Opinion from corresponding PCT application No. PCT/US2014/049662 dated Oct. 16, 2014; 12 pages.

*Primary Examiner* — Courtney Thomas
(74) *Attorney, Agent, or Firm* — Lucas Divine; General Electric Company

(57) ABSTRACT

A CT system includes an x-ray source, a high-voltage (HV) tank coupled to the x-ray source, and an inverter coupled to the HV tank. The inverter includes an H-bridge configuration of switches comprising a first leg and a second leg, wherein the first and second legs include respective upper and lower switches, and at least one additional leg of switches having respective upper and lower switches. The system includes a controller configured to interleave switch operation between the H-bridge configuration and the at least one additional leg of switches.

21 Claims, 5 Drawing Sheets

INTERLEAVED RESONANT CONVERTER

BACKGROUND

This disclosure relates generally to diagnostic imaging and, more particularly, to improved power conversion for a computed tomography (CT) system.

Typically, in computed tomography (CT) imaging systems, an x-ray source emits a fan or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are transmitted to the data processing system for image reconstruction. Imaging data may be obtained using x-rays that are generated at a single polychromatic energy. However, some systems may obtain multi-energy images that provide additional information for generating images, and therefore include fast switching of x-ray tube kV between two discrete levels of, for instance, 80 and 140 kV. And, it is generally desired to have a crisp transition between the high and low frequencies and if the switching is too slow, blurring can occur in reconstructed images.

The x-ray generator of a CT system is typically located within the gantry and, as such, rotates about an imaging bore during data acquisition on a rotatable side of the gantry. The x-ray generator includes the x-ray source, a high voltage (HV) tank, and an inverter that is operationally connected to a slip ring. External to the slip ring and on the stationary side of the gantry is a power distribution unit (PDU). The inverter is typically fed with a DC voltage, for example, 650 VDC, and generates an AC waveform of, for example, approximately 300 VAC, at a frequency of typically 20-50 kHz. The AC frequency is fed to the HV tank, which has a transformer and rectifiers that develop a DC HV potential. The HV potential is applied to the x-ray source.

According to one known configuration, the inverter is positioned on the rotating base and therefore rotates with data acquisition components. The inverter includes, in one known arrangement, a full-bridge or "H" configuration of four (4) power switches that switch in a pattern to control the inverter current, and thus output power of the converter. The full-bridge includes two legs, each of which includes an upper and a lower switch. The switches are typically insulated-gate bipolar transistors or IGBTs. In this known configuration of four power switches, switching in the two legs is controlled in a pattern such that either the upper or lower switch of each leg is on. The switching between on and off is controlled in such a fashion that a high-frequency inverter current is formed, which is in turn fed to the HV tank, as stated. One known switching frequency of a four-switch design is 50 kHz, however as detector scintillator technology and other system operating parameters have increased, so too has the need to operate at a higher frequency.

Power converter performance is generally limited due to its maximum switching frequency, which is a function of the switch technology used. Further, some converters are designed to provide a changing output voltage waveform, the fidelity of which is limited by the switching frequency (e.g., fast kV switching for dual energy imaging). Increasing the switching frequency may allow decreasing magnetic core area needed for a given power. Some known converters use switching devices that includes MOSFETS and silicon carbide MOSFETS, but such devices are relatively very expensive and can be difficult to package.

Therefore, it would be desirable to have an improved resonant converter in a CT system.

BRIEF DESCRIPTION

Embodiments are directed toward a method and apparatus to improve a resonant converter in a CT system.

According to one aspect, a CT system includes an x-ray source, a high-voltage (HV) tank coupled to the x-ray source, and an inverter coupled to the HV tank. The inverter includes an H-bridge configuration of switches comprising a first leg and a second leg, wherein the first and second legs include respective upper and lower switches, and at least one additional leg of switches having respective upper and lower switches. The system includes a controller configured to interleave switch operation between the H-bridge configuration and the at least one additional leg of switches.

According to another aspect, a method of manufacturing a CT system includes coupling an x-ray source to a high-voltage (HV) tank, and coupling an inverter to the HV tank. The inverter includes an H-bridge configuration of switches comprising a first leg and a second leg, wherein the first and second legs include respective upper and lower switches, and at least one additional leg of switches having respective upper and lower switches. The method includes configuring a controller to interleave switch operation between the H-bridge configuration and the at least one additional leg of switches.

According to yet another aspect, an inverter for a CT system includes an H-bridge configuration of switches comprising a first leg and a second leg, wherein the first and second legs include respective upper and lower switches, and at least one additional leg of switches having respective upper and lower switches. The switches are controllable to interleave switch operation between the H-bridge configuration and the at least one additional leg of switches.

Various other features and advantages will be made apparent from the following detailed description and the drawings.

DETAILED DESCRIPTION

The operating environment of disclosed embodiments is described with respect to a sixty-four-slice computed tomography (CT) system. However, it will be appreciated by those skilled in the art that embodiments are equally applicable for use with other multi-slice configurations. Moreover, disclosed embodiments will be described with respect to the detection and conversion of x-rays. However, one skilled in the art will further appreciate that embodiments are equally applicable for the detection and conversion of other high frequency electromagnetic energy. Disclosed embodiments will be described with respect to a "third generation" CT scanner, but is equally applicable with other CT systems as well as vascular and surgical C-arm systems and other x-ray tomography systems. Further, it is contemplated that the disclosed subject matter is applicable to other imaging systems, such as magnetic resonance (MR) imaging, and x-ray systems, as examples.

Figure 1:
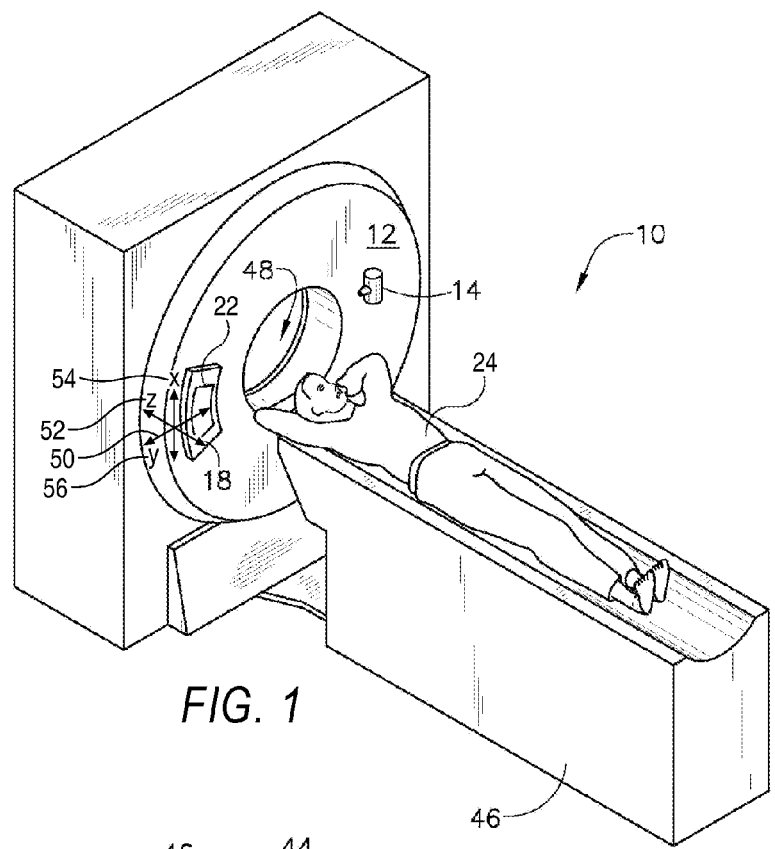
FIG. 1 is a pictorial view of a CT imaging system that incorporates disclosed embodiments.
Figure 2:
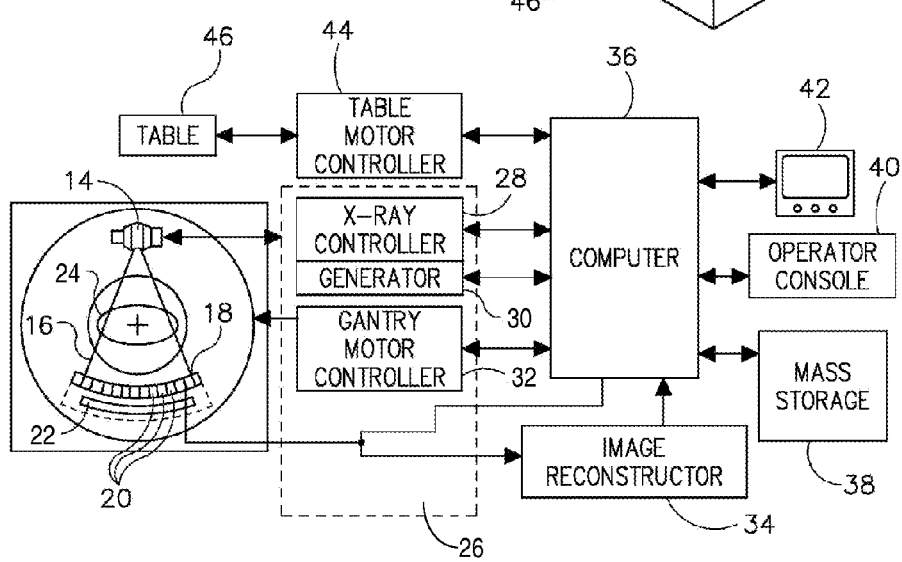
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. X-ray source 14 includes either a stationary target or a rotating target. Detector assembly 18 is formed by a plurality of detectors 20 data acquisition systems (DAS) 22. The plurality of detectors 20 sense the projected x-rays that pass through a medical patient 24, and DAS 22 converts the data to digital signals for subsequent processing. Each detector 20 produces an analog electrical signal that represents the intensity of an impinging x-ray beam and hence the attenuated beam as it passes through patient 24. During a scan to acquire x-ray projection data, gantry 12 and the components mounted thereon, on a rotatable base, rotate about a center of rotation.

Rotation of gantry 12 and the operation of x-ray source 14 are governed by a control mechanism 26 of CT system 10. Control mechanism 26 includes an x-ray controller 28 and generator 30 that provides power and timing signals to x-ray source 14 and a gantry motor controller 32 that controls the rotational speed and position of gantry 12. An image reconstructor 34 receives sampled and digitized x-ray data from DAS 22 and performs high speed image reconstruction. The reconstructed image is applied as an input to a computer 36 which stores the image in a mass storage device 38.

Computer 36 also receives commands and scanning parameters from an operator via an operator console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position patient 24 and gantry 12. Particularly, table 46 moves patients 24 through a gantry opening 48 in whole or in part. A coordinate system 50 for detector assembly 18 defines a patient or Z-axis 52 along which patient 24 is moved in and out of opening 48, a gantry circumferential or X-axis 54 along which detector assembly 18 passes, and a Y-axis 56 that passes along a direction from a focal spot of X-ray source 14 to detector assembly 18.

X-ray source 14, in accordance with present embodiments, is configured to emit x-rays or x-ray beam 16 at one or more energies. For example, x-ray source 14 may be configured to switch between relatively low energy polychromatic emission spectra (e.g., at approximately 80 kVp) and relatively high energy polychromatic emission spectra (e.g., at approximately 140 kVp). As will be appreciated, x-ray source 14 may also be operated so as to emit x-rays at more than two different energies. Similarly, x-ray source 14 may emit at polychromatic spectra localized around energy levels (i.e., kVp ranges) other than those listed herein (e.g., 100 kVP, 120 kVP, etc.). Selection of the respective energy levels for emission may be based, at least in part, on the anatomy being imaged.

In some embodiments X-ray controller 28 may be configured to selectively activate x-ray source 14 such that tubes or emitters at different locations within system 10 may be operated in synchrony with one another or independent of one another. In certain embodiments discussed herein, the x-ray controller 28 may be configured to provide fast-kVp switching of x-ray source 14 so as to rapidly switch source 14 to emit X-rays at the respective polychromatic energy spectra in succession during an image acquisition session. For example, in a dual-energy imaging context, x-ray controller 28 may operate x-ray source 14 so that x-ray source 14 alternately emits x-rays at the two polychromatic energy spectra of interest, such that adjacent projections are acquired at different energies (i.e., a first projection is acquired at high energy, the second projection is acquired at low energy, the third projection is acquired at high energy, and so forth). In one such implementation, fast-kVp switching operation performed by x-ray controller 28 yields temporally registered projection data. In some embodiments, other modes of data acquisition and processing may be utilized. For example, a low pitch helical mode, rotate-rotate axial mode, N×M mode (e.g., N low-kVp views and M high-kVP views) may be utilized to acquire dual-energy datasets.

Figure 3:
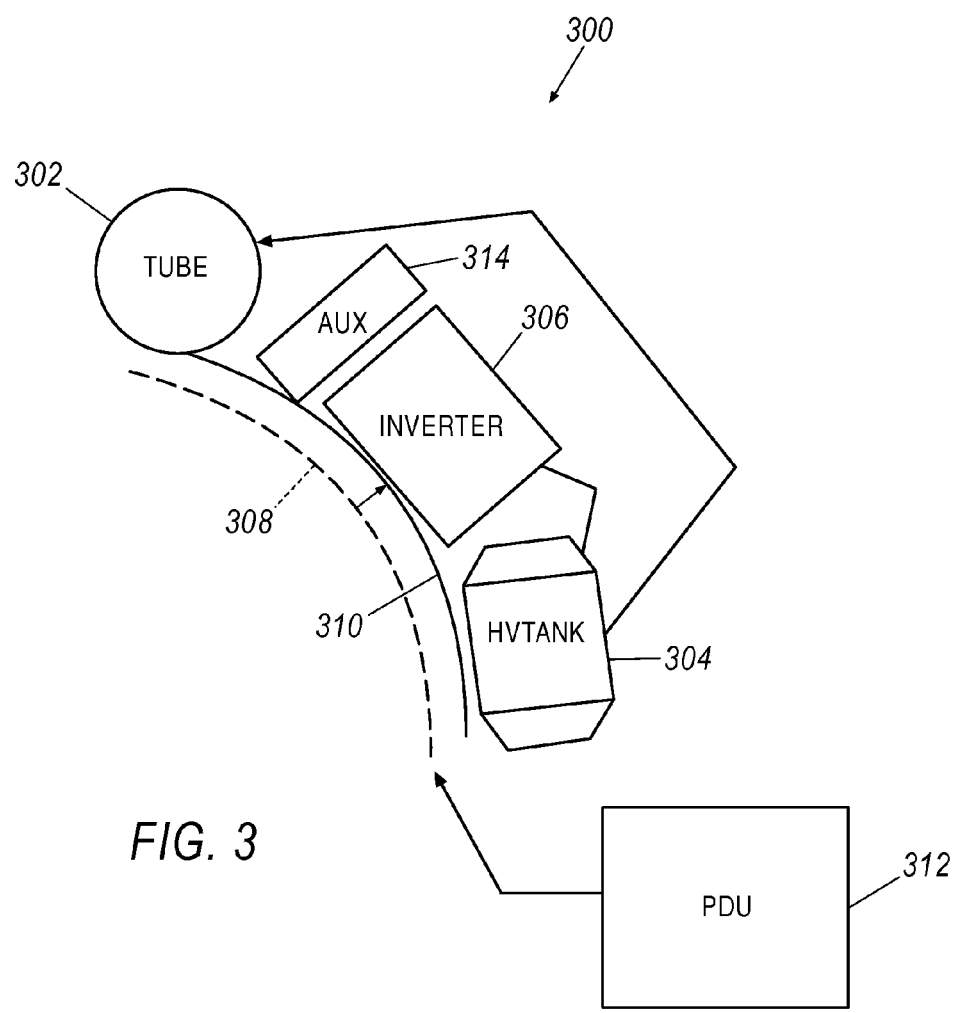
FIG. 3 is a schematic of an x-ray generator and slip ring configuration for a CT imaging system such as illustrated in FIGS. 1 and 2.

Referring to FIG. 3, an x-ray generator of a CT system is located within the gantry and, as such, rotates around an imaging bore during data acquisition, and the gantry includes a rotatable base and an opening for receiving an object to be scanned. The x-ray generation generally includes an x-ray tube, data acquisition system, and an arcuate shaped detector array or assembly that is positioned to receive x-rays from the x-ray source. The x-ray generator and slip ring configuration 300 includes an x-ray source or tube 302, a high voltage (HV) tank 304, and an inverter 306 operationally connected to a slip ring 308. X-ray tube 302, HV tank 304, and inverter 306 are each connected and secured to a rotating base 310 that supports each during rotation of the gantry. External to rotating base 310 and electrically connected to slip ring 308 is a power distribution unit (PDU) 312 that is stationary and therefore does not rotate with x-ray tube 302, tank 304, and inverter 306. Inverter 306 is typically fed with a DC voltage, for example, 650 VDC, and generates an AC voltage waveform, for example, approximately 300 VAC, at a specified frequency, e.g. 20 k 50 kHz. The AC voltage is then fed to the HV tank 304 which has a transformer and rectifiers (not shown) that develop a DC HV potential. The HV potential is then applied to the x-ray tube 302. Rotating base 310 is also designed with one or more auxiliary devices 314 that may include auxiliary power devices. As such, inverter 306, HV tank 304, and X-ray tube 302 are positioned on the rotating side of slip ring 308. As such, a relatively low DC voltage is supplied to slip ring 308 which is then transferred to inverter 306 for conditioning. FIG. 3 illustrates one exemplary embodiment in which inverter 306 is positioned on rotating base 310. However, in another example (not shown) inverter 306 is external to slip ring 308 and on a stationary side of the gantry.

Figure 4:
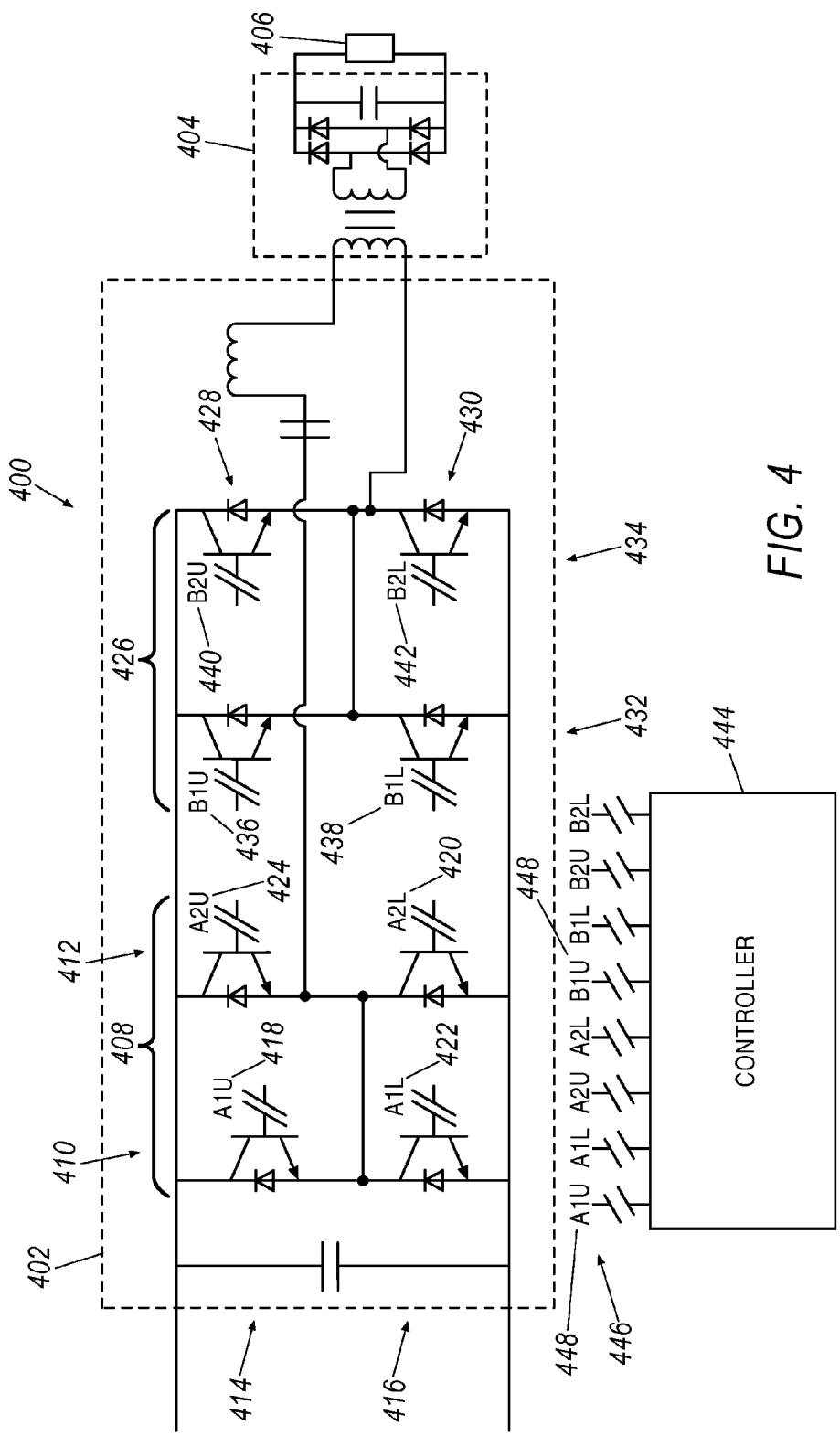
FIG. 4 is an illustration of an inverter circuit for a CT imaging system such as illustrated in FIGS. 1 and 2.

Referring to FIG. 4, an inverter circuit 400 is shown that includes an inverter 402, a high-voltage (HV) tank 404, and an x-ray tube or source 406, which correspond generally to the components illustrated in FIG. 3. According to one embodiment, inverter circuit 400 is positioned in a CT system, such as system 10 of FIGS. 1 and 2, to provide a high-frequency inverter current by selective operation or interleaving of switches to increase inverter frequency and reduce power dissipation. Circuit 400 may otherwise be referred to as a "series-resonant converter" or an interleaved resonant converter for powering CT and other imaging devices, and includes HV tank 404 coupled to x-ray source 406, and inverter 402 coupled to HV tank 404. Inverter 402 includes an H-bridge configuration of switches 408 that includes a first leg 410 and a second leg 412.

First and second legs 410, 412 include respective upper switches 414 and lower switches 416. Thus, in one example, switch "A1U" 418 of switches 408 is in first leg 410, and is an upper switch of upper switches 414. As another example, switch "A2L" 420 of switches 408 is in second leg 412, and is a lower switch of lower switches 416. Similarly, switches A1L 422 and A2U 424 are included as switches 408. As such, H-bridge switches 410, 432 include, in the illustrated embodiment, only 4 switches 418, 422, 436, and 438.

Inverter 402 includes at least one additional leg of switches 412, 434 having respective upper switches 424, 428 and lower switches 420, 430. The at least one additional leg of switches 412, 434, in the illustrated embodiment, includes a second H-bridge configuration of switches 412, 434 that includes a third leg 412 and a fourth leg 434. The third and fourth legs 412, 434 include respective upper and lower switches 428, 430, as described, and thus in the illustrated example also includes 4 switches 424, 420, 440, and 442. However, it is contemplated that second switches 412, 434 may include only one leg of switches, such as third leg 434, which can be interleaved in operation along with switches 410, 432 according to another embodiment. In one embodiment, the switches of the H-bridge configuration 410, 432 and of the at least one additional leg 434 are insulated-gate bipolar transistors (IGBTs).

A controller 444 is coupled to switches 418-424 and 436-442, and is configured to interleave switch operation between H-bridge configuration 410, 432 and the at least one additional leg of switches 412, 434. Controller 444 includes control lines 446 that are each coupled to respective switches 418-424 and 436-442. To simplify the illustration and details of FIG. 4, control lines 446 are illustrated in abbreviated format, but it is understood that they are each connected to respective switches to control their on-off operation and interleaves their operation. For instance, switch "A1U" 418 is controlled by its respective "A1U" control line, shown as element 448. As another example, switch "B1U" 436, in the at least one additional leg of switches 426 and in third leg 432 and upper switches 428 thereof, is controlled by control line 448 that is also designated having a "B1U" designation. All switches illustrated 418-424 and 436-442 have a corresponding control line.

Figure 5:
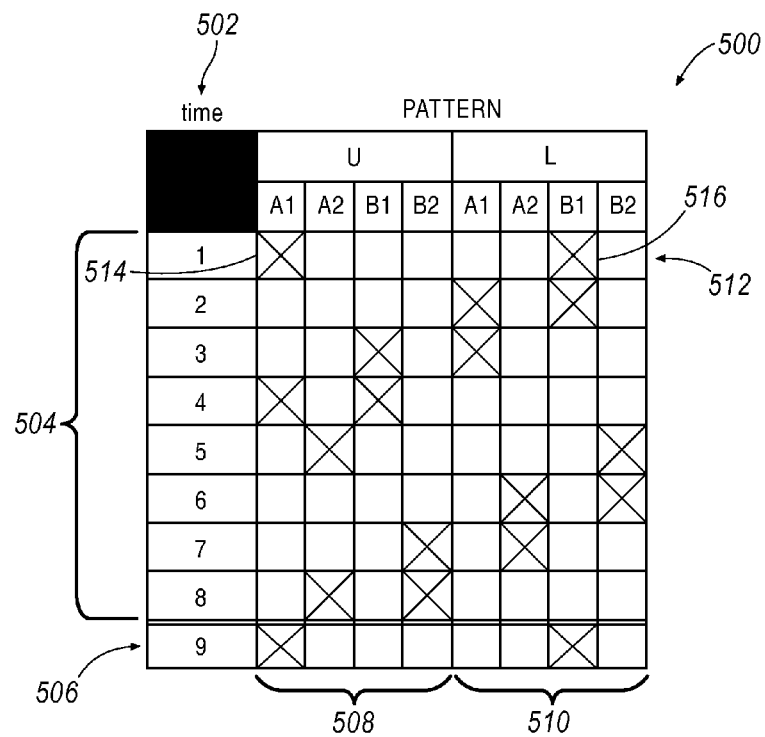
FIG. 5 illustrates a pattern of switch operation, for switches illustrated in FIG. 4.

Referring to FIG. 5, controller 444 of FIG. 4 is configured to interleave switch operation such that one of the H-bridge and one of the at least one additional leg of switches is on, according to pattern 500. Pattern 500 includes a series of time steps 502 that includes a first 8 steps 504 of a pattern, and then step 9 506 in the illustrated pattern begins a repeat of pattern 500. Pattern 500 includes four upper switches 508 and four lower switches 510, designated respectively as "U" and "L" at the top of the figure. Upper switches 508 in pattern 500 include A1, A2, B1, and B2 switches. Likewise, lower switches 510 in pattern 500 also include A1, A2, B1, and B2 switches. As such, the eight combinations of upper, lower, and A1, A2, B1, and B2 switches correspond to the eight switches 418-424 and 436-442 of FIG. 4. Pattern 500 thus illustrates, in each box marked with an "X", which switches are on (and those not marked are, correspondingly, off). For instance, at time step "1" 512, an "X" is included in box "A1U" 514, and an "X" is also included in box "B1L" 516. The switches that are "on" (514, 516) therefore correspond to switches A1U 418 and B1L 438 of FIG. 4. As such, stepping through time steps 502, controller 444 follows pattern 500 by selectively turning on and off switches to interleave operation of inverter 402.

Thus, controller 444 is configured to cycle the switches, according to pattern 500, such that either the upper or the lower of both the 1) H-bridge, and 2) the at least one additional leg of switches, are on. That is, as can be seen in the pattern 500 and in the corresponding switches of FIG. 4, at all timesteps an "A" and a "B" switch are on, but the pattern is switched such that an interleaved current results. And, as stated, at step 9 506 the pattern repeats and corresponds to step 1 512.

Figure 6:
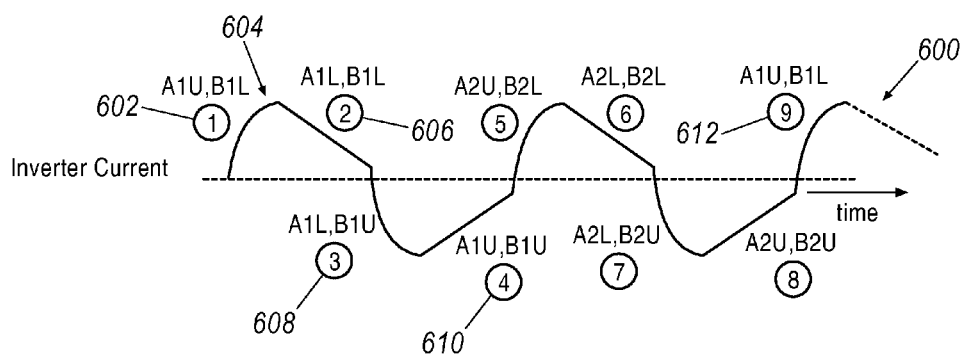
FIG. 6 illustrates a resulting current waveform that corresponds to the switches of FIG. 4 and the pattern of FIG. 5.

It is understood that the switch or corresponding diode will be on, depending on current direction. Referring now to FIG. 6, a resulting current pattern 600 is illustrated that corresponds to the switches of FIG. 4 and the pattern of FIG. 5. Resulting pattern 600 corresponds to the nine timesteps of pattern 500. For instance, at timestep 1 512, corresponding to "time 1" 602 when switches A1U and B1L are on, a current waveform 604 results during that time period. Similarly, as pattern 500 is followed and the switches of inverter 402 are operated accordingly by controller 444, the inverter current is formed during the corresponding timesteps of 2, 3, 4, etc . . . 606, 608, 610, etc . . . , and as stated the pattern repeats beginning at step 9 612.

Further, although a specific set of switches are shown in FIG. 4, and a specific pattern of switch operation is shown in FIG. 5, it is contemplated that other switch arrangements and corresponding patterns of operation may be included within the scope of this disclosure. Thus, by providing additional switches for interleaving, the switching frequency can be increased proportionally by the number of additional legs. In one example, the kV switch transition times have been decreased 3× from 100 us to 32 us. Also, the higher converter operating frequency has a benefit of shrinking the size of magnetic material needed for a transformer. This has been used to reduce the size of the high frequency PDU transformer. Additionally, power converters may be limited in power output due to the power dissipation in the switching devices. By interleaving, the power dissipation is spread equally among the switch legs (which may not be experienced in parallel-operating devices). As such, the disclosed interleaving technique allows higher frequency converter switching which lowers CT kV switching rise and fall times. This reduction in rise/fall times can either improve temporal resolution of the dual energy data or be used to reduce dose needed for CT dual energy scanning This technique may also be used to achieve ultra-fast kV rise and fall times needed for higher speed gantry operation. Thus, with faster switching rates achieved using the disclosed technique, more fidelity is experienced, resulting in faster kV switching, that allows higher bandwidth control.

Disclosed herein also is a method of manufacturing a CT system 10, in accordance with the disclosed system having inverter circuit 400 above. The method includes coupling an x-ray source 406 to a high-voltage (HV) tank 404, and coupling an inverter 402 to the HV tank 404. The inverter 402 includes an H-bridge configuration of switches 410, 432 that includes a first leg 410 and a second leg 432. The first and second legs 410, 432 include respective upper and lower switches 414, 416, and at least one additional leg of switches 412, 434 having respective upper and lower switches 428, 430. The method includes configuring a controller, such as controller 444 to interleave switch operation between the H-bridge configuration 410, 432 and the at least one additional leg of switches 412, 434.

The method includes configuring the controller 444 to interleave switch operation such that one of the switches of H-bridge switches 410, 432 and one of the at least one additional leg of switches 410, 434 is on, and further includes configuring the controller to cycle the switches such that either the upper or the lower of both the 1) H-bridge, and 2) the at least one additional leg of switches, are on, such as is illustrated in pattern 500.

Figure 7:
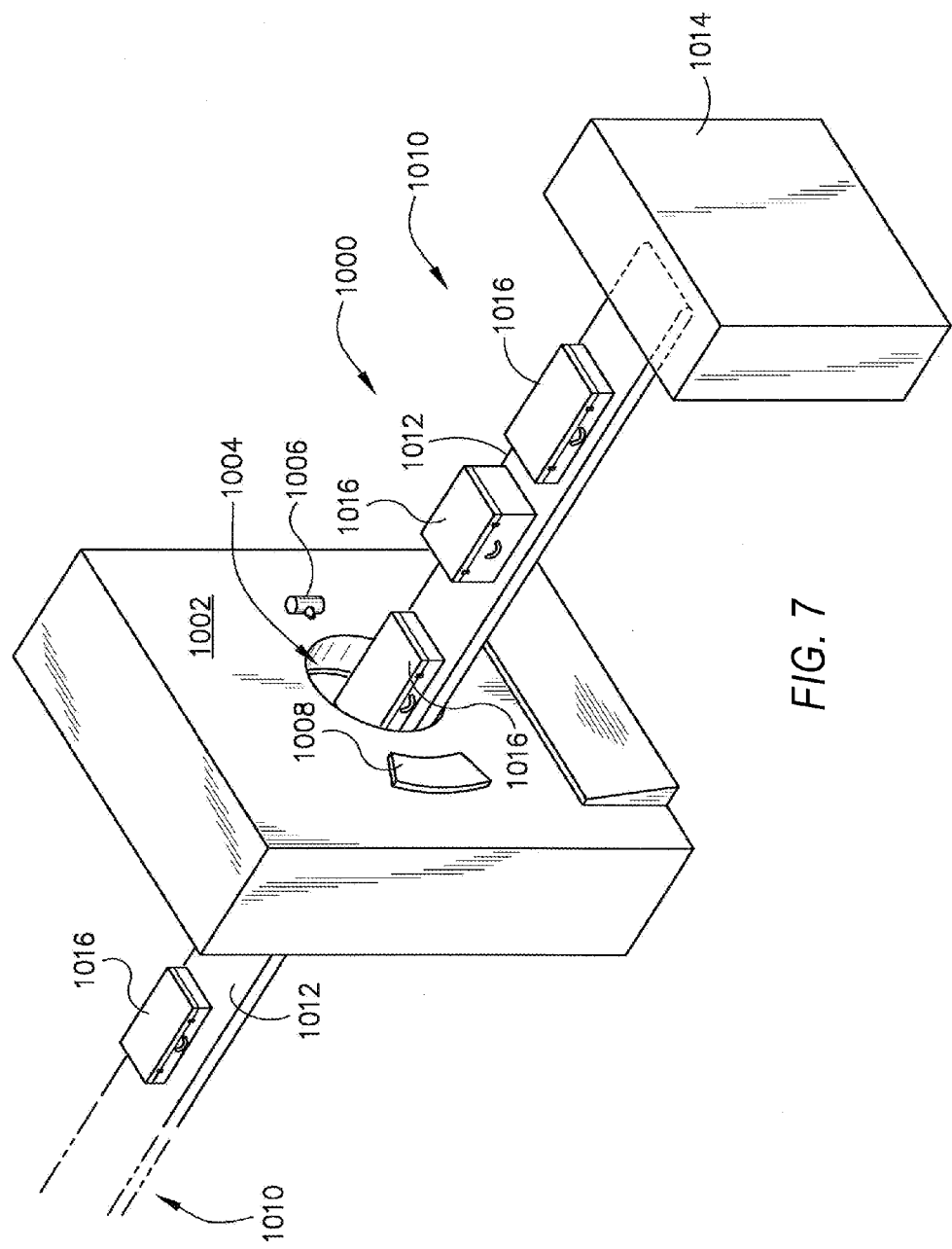
FIG. 7 is a pictorial view of a CT system for use with a non-invasive package inspection system according to an embodiment.

Referring now to FIG. 7, there is shown a package/baggage inspection system 1000 that can use the image acquisition and reconstructions techniques according to embodiments disclosed and which includes a rotatable gantry 1002 having an opening 1004 therein through which packages or pieces of baggage may pass. The rotatable gantry 1002 houses one or more x-ray energy sources 1006 as well as a detector assembly 1008 having scintillator arrays comprised of scintillator cells. A conveyor system 1010 is also provided and includes a conveyor belt 1012 supported by structure 1014 to automatically and continuously pass packages or baggage pieces 1016 through opening 1004 to be scanned. Objects 1016 are passed through opening 1004 by conveyor belt 1012, imaging data is then acquired, and the conveyor belt 1012 removes the packages 1016 from opening 1004 in a controlled and continuous manner. As a result, postal inspectors, baggage handlers, and other security personnel may non-invasively inspect the contents of packages 1016 for explosives, knives, guns, contraband, etc.

An implementation of system 10 and/or 1000 in an example comprises a plurality of components such as one or more of electronic components, hardware components, and/or computer software components. A number of such components can be combined or divided in an implementation of the system 10 and/or 1000. An exemplary component of an implementation of the system 10 and/or 1000 employs and/or comprises a set and/or series of computer instructions written in or implemented with any of a number of programming languages, as will be appreciated by those skilled in the art. An implementation of system 10 and/or 1000 in an example comprises any (e.g., horizontal, oblique, or vertical) orientation, with the description and figures herein illustrating an exemplary orientation of an implementation of the system 10 and/or 1000, for explanatory purposes.

An implementation of system 10 and/or system 1000 in an example employs one or more computer readable signal bearing media. A computer-readable signal-bearing medium in an example stores software, firmware and/or assembly language for performing one or more portions of one or more implementations. An example of a computer-readable signal-bearing medium for an implementation of the system 10 and/or the system 1000 comprises the recordable data storage medium of the image reconstructor 34, and/or mass storage device 38 of computer 36. A computer-readable signal-bearing medium for an implementation of the system 10 and/or the system 1000 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 1000, for instance, one or more of a telephone network, a local area network ("LAN"), a wide area network ("WAN"), the Internet, and/or a wireless network.

According to one embodiment, a CT system includes an x-ray source, a high-voltage (HV) tank coupled to the x-ray source, and an inverter coupled to the HV tank. The inverter includes an H-bridge configuration of switches comprising a first leg and a second leg, wherein the first and second legs include respective upper and lower switches, and at least one additional leg of switches having respective upper and lower switches. The system includes a controller configured to interleave switch operation between the H-bridge configuration and the at least one additional leg of switches.

According to another embodiment, a method of manufacturing a CT system includes coupling an x-ray source to a high-voltage (HV) tank, and coupling an inverter to the HV tank. The inverter includes an H-bridge configuration of switches comprising a first leg and a second leg, wherein the first and second legs include respective upper and lower switches, and at least one additional leg of switches having respective upper and lower switches. The method includes configuring a controller to interleave switch operation between the H-bridge configuration and the at least one additional leg of switches.

According to yet another embodiment, an inverter for a CT system includes an H-bridge configuration of switches comprising a first leg and a second leg, wherein the first and second legs include respective upper and lower switches, and at least one additional leg of switches having respective upper and lower switches. The switches are controllable to interleave switch operation between the H-bridge configuration and the at least one additional leg of switches.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the preceding discussion is generally provided in the context of medical imaging, it should be appreciated that the present techniques are not limited to such medical contexts. The provision of examples and explanations in such a medical context is to facilitate explanation by providing instances of implementations and applications. The disclosed approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

While the disclosed subject matter has been described in detail in connection with only a limited number of embodiments, it should be readily understood that the disclosure is not limited to such disclosed embodiments. Rather, that disclosed can be modified to incorporate any number of variations, alterations, substitutions or equivalent arrangements not heretofore described, but which are commensurate with the spirit and scope of the disclosure. Furthermore, while single energy and dual-energy techniques are discussed above, that disclosed encompasses approaches with more than two energies. Additionally, while various embodiments have been described, it is to be understood that disclosed aspects may include only some of the described embodiments. Accordingly, that disclosed is not to be seen as limited by the foregoing description, but is only limited by the scope of the appended claims.

What is claimed is:

1. A CT system comprising:
    an x-ray source;
    a high-voltage (HV) tank coupled to the x-ray source; and
    an inverter coupled to the HV tank, wherein the inverter comprises:
        an H-bridge configuration of switches comprising a first leg and a second leg, wherein the first and second legs include respective upper and lower switches; and
        at least one additional leg of switches having respective upper and lower switches; and
    a controller configured to interleave switch operation between the H-bridge configuration and the at least one additional leg of switches.

2. The CT system of claim 1, wherein the H-bridge includes only 4 switches.

3. The CT system of claim 1, wherein the at least one additional leg of switches is a second H-bridge configuration of switches comprising a third leg and a fourth leg, wherein the third and fourth legs include respective upper and lower switches.

4. The CT system of claim 1, wherein the controller is configured to interleave switch operation such that one of the H-bridge and one of the at least one additional leg of switches is on.

5. The CT system of claim 4, wherein the controller is further configured to cycle the switches such that either the upper or the lower of both the 1) H-bridge, and 2) the at least one additional leg of switches, are on.

6. The CT system of claim 1, further comprising:
    a gantry having a rotatable base and having an opening for receiving an object to be scanned; and
    an arcuate detector assembly positioned to receive x-rays from the x-ray source.

7. The CT system of claim 1, wherein the switches of the H-bridge configuration and of the at least one additional leg are insulated-gate bipolar transistors (IGBTs).

8. A method of manufacturing a CT system, comprising:
    coupling an x-ray source to a high-voltage (HV) tank;
    coupling an inverter to the HV tank, the inverter having:
        an H-bridge configuration of switches comprising a first leg and a second leg, wherein the first and second legs include respective upper and lower switches; and
        at least one additional leg of switches having respective upper and lower switches; and
    configuring a controller to interleave switch operation between the H-bridge configuration and the at least one additional leg of switches.

9. The method of claim 8, wherein the H-bridge includes only 4 switches.

10. The method of claim 8, wherein the at least one additional leg of switches is a second H-bridge configuration of switches comprising a third leg and a fourth leg, wherein the third and fourth legs include respective upper and lower switches.

11. The method of claim 8, further comprising configuring the controller to interleave switch operation such that one of the H-bridge and one of the at least one additional leg of switches is on.

12. The method of claim 11, further comprising configuring the controller to cycle the switches such that either the upper or the lower of both the 1) H-bridge, and 2) the at least one additional leg of switches, are on.

13. The method of claim 8, further comprising:
    providing a gantry having a rotatable base and having an opening for receiving an object to be scanned; and
    coupling an arcuate detector assembly to the gantry that is positioned to receive x-rays from the x-ray source.

14. An inverter, comprising:
    an H-bridge configuration of switches comprising a first leg and a second leg, wherein the first and second legs include respective upper and lower switches; and
    at least one additional leg of switches having respective upper and lower switches; and
    wherein the switches are controllable to interleave switch operation between the H-bridge configuration and the at least one additional leg of switches.

15. The inverter of claim 14, wherein the H-bridge includes only 4 switches.

16. The inverter of claim 14, wherein the at least one additional leg of switches is a second H-bridge configuration of switches comprising a third leg and a fourth leg, wherein the third and fourth legs include respective upper and lower switches.

17. The inverter of claim 14, wherein the switches are controllable to interleave switch operation such that one of the H-bridge and one of the at least one additional leg of switches is on.

18. The inverter of claim 17, wherein the switches are further controllable such that either the upper or the lower of both the 1) H-bridge, and 2) the at least one additional leg of switches, are on.

19. The inverter of claim 14, wherein the inverter is positionable on a gantry, the gantry having a rotatable base and having an opening for receiving an object to be scanned, and an arcuate detector assembly is positioned to receive x-rays from the x-ray source.

20. The inverter of claim 14, wherein the switches of the H-bridge configuration and of the at least one additional leg are insulated-gate bipolar transistors (IGBTs).

21. The inverter of claim 14, wherein the inverter is positionable in one of a computed tomography (CT) system, a magnetic resonance (MR) system, and an x-ray system.

* * * * *